United States Patent [19]

McKinnie et al.

[11] Patent Number: 5,283,375
[45] Date of Patent: Feb. 1, 1994

[54] PROCESS FOR HIGH PURITY TETRABROMOBISPHENOL-A

[75] Inventors: Bonnie G. McKinnie; Gary L. Sharp; Robert E. Williams, all of Magnolia, Ark.

[73] Assignee: Ethyl Corporation, Richmond, Va.

[21] Appl. No.: 990,414

[22] Filed: Dec. 15, 1992

Related U.S. Application Data

[63] Continuation-in-part of Ser. No. 861,544, Apr. 1, 1992, Pat. No. 5,208,389.

[51] Int. Cl.$^5$ ............... C07C 39/38; C07C 39/367
[52] U.S. Cl. ............... 568/726; 568/722; 568/723; 568/776; 568/779
[58] Field of Search ............... 568/726, 723, 776, 779, 568/722, 724

[56] References Cited

U.S. PATENT DOCUMENTS

| | | | |
|---|---|---|---|
| 3,029,291 | 4/1962 | Dietzler | 260/619 |
| 3,182,088 | 5/1965 | Hennis | 260/619 |
| 3,546,302 | 12/1970 | Asadorian et al. | 260/619 |
| 3,868,423 | 2/1975 | Montanari et al. | 260/619 |
| 3,929,907 | 12/1975 | Janzon et al. | 260/619 |
| 4,075,119 | 2/1978 | Schmidt et al. | 252/182 |
| 4,112,242 | 9/1978 | Swietoslawski et al. | 568/726 |
| 4,180,684 | 12/1979 | Kleinschmit et al. | 568/726 |
| 4,210,765 | 7/1980 | Mark | 568/726 |
| 4,283,566 | 8/1981 | Mark | 568/726 |
| 4,451,675 | 5/1984 | Bounds | 568/726 |
| 4,628,124 | 12/1986 | McKinnie et al. | 568/726 |
| 4,701,568 | 10/1987 | McKinnie et al. | 568/726 |
| 4,783,556 | 11/1988 | Mitchell et al. | 568/726 |
| 4,909,997 | 3/1990 | Mitchell et al. | 422/225 |
| 4,990,321 | 2/1991 | Sato et al. | 423/486 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/726 |
| 5,059,726 | 10/1991 | Eguchi et al. | 568/726 |
| 5,068,463 | 11/1991 | Walter | 568/726 |
| 5,107,035 | 4/1992 | Hines | 568/726 |
| 5,138,103 | 8/1992 | Eguchi et al. | 568/726 |

FOREIGN PATENT DOCUMENTS

| | | |
|---|---|---|
| 686772 | 5/1964 | Canada ............... 568/726 |
| 706433 | 5/1964 | Canada ............... 568/726 |
| 0380363 | 8/1990 | European Pat. Off. . |
| 2005259 | 8/1971 | Fed. Rep. of Germany . |
| 2274586 | 1/1976 | France . |
| 64410 | 3/1985 | Israel . |
| 225034 | 12/1983 | Japan . |
| 58728 | 12/1985 | Japan . |
| 48641 | 3/1987 | Japan . |
| 316748 | 12/1988 | Japan . |
| 949306 | 2/1964 | United Kingdom . |

OTHER PUBLICATIONS

Chemical Abstract No. 110003e vol. 109(13) Sep. 26, 1988.

(List continued on next page.)

Primary Examiner—Werren B. Lone
Attorney, Agent, or Firm—David E. LaRose

[57] ABSTRACT

This invention relates to a process for preparing a flame retardant product predominant in tetrabromobisphenol-A. The process comprises: (a) dissolving bisphenol-A in a methanol solvent containing up to about 5 weight percent water, wherein the ratio of methanol to bisphenol-A ranges from about 25 to about 43 moles of methanol per mole of bisphenol-A based on the total amount of methanol used and the total amount of bisphenol-A to be brominated; (b) adding to the solution in (a) from about 3.9 to about 4.2 moles of bromine per mole of bisphenol-A to be brominated while maintaining a reaction temperature in the range of from about 0° to about 40° C.; (c) after the bromination is substantially complete, adding water to precipitate the tetrabromobisphenol-A thus formed; and (d) purifying the precipitated tetrabromobisphenol-A so as to obtain a product predominant in tetrabromobisphenol-A containing less than about 20 ppm total ionic impurity.

27 Claims, No Drawings

OTHER PUBLICATIONS

Chemical Abstract No. 174372c vol. 110(20) May 15, 1989.

Chemical Abstract No. 173951d vol. 110(20) May, 15, 1989.

Chemical Abstract No. 177054b vol. 85(23) Dec. 6, 1976.

Chemical Abstract No. 189500c vol. 86(25) Jun. 20, 1977.

Sharma, et al, "Copolycarbonates of bisphenol A and tetrahalo bisphenols A: Synthesis of tetrahalobisphenols-A: Part I", *Popular Plastics & Rubber*, 26(1), pp. 3–9, (1981).

Islam, et al, "Tetrahalogenated 4:4'-Dihydroxydiphenylalkanes, their Synthesis and some of their Reactions", *Egypt. J. Chem.*, vol. 20(5), pp. 483–490, (1977).

Sadygov, et al, "Oxidative bromination of 2,2-bis(-4'-hydroxyphenyl)propane", *Neftekhimiya*, 30(1), pp. 109–113, (1990).

Chemical Abstract No. 231164b vol. 101(26) Dec. 24, 1984.

Chemical Abstract No. 62672d vol. 102(8) Feb. 25, 1985.

Chemical Abstract No. 79427a vol. 102(No. 8) Feb. 25, 1985.

Chemical Abstract No. 155068p vol. 105(No. 18) Nov. 3, 1986.

PROCESS FOR HIGH PURITY TETRABROMOBISPHENOL-A

This application is a continuation-in-part of copending application Ser. No. 861,544, filed Apr. 1, 1992, U.S. Pat. No. 5,208,389.

BACKGROUND

This invention relates to a process for preparing tetrabromobis-phenol-A and to an improvement in a process for enhancing the purity of a flame retardant product predominant in a tetrabromobisphenol-A.

4,4'-isopropylidenebis(2,6-dibromophenol) is a well known commercial flame retardant and is usually referred to as tetrabromobisphenol-A (hereinafter "TBBPA"). Products comprised predominantly of TBBPA are useful as flame retardants in many macromolecular formulations. The literature is replete with processes for the manufacture of TBBPA, see, for example, U.S. Pat. No. 3,029,291; U.S. Pat. No. 3,182,088; U. S. Pat. No. 3,234,289; U.S. Pat. No. 3,363,007; 3,546,302; U.S. Pat. No. 3,868,423; U.S. Pat. No. 3,929,907; U.S. Pat. No. 4,013,728; U.S. Pat. No. 4,036,894; U.S. Pat. No. 4,112,242; U.S. Pat. No. 4,180,684; U.S. Pat. No. 4,431,847; U.S. Pat. No. 4,451,675; U.S. Pat. No. 4,701,568; U.S. Pat. No. 4,990,321; U.S. Pat. No. 5,008,469; U.S. Pat. No. 5,059,726; U.S. Pat. No. 5,068,463; Japanese Kokai 2 (1990) 196,747; EPO 380,363; British Patent 949,306. Processes which produce a TBBPA predominant product having a particularly low organic impurity content are described in U.S. Pat. No. 4,628,124; U.S. Pat. No. 4,783,556; U.S. Pat. No. 4,909,997; U.S. Pat. No. 5,017,728; U.S. Pat. No. 5,059,722, and U.S. Pat. No. 5,138,103 incorporated herein by reference as if fully set forth. Most if not all of the foregoing processes describe the recovery of TBBPA from the reaction mass by adding water to precipitate the product.

While the processes described in the foregoing patents yield products which are useful for most flame retardant applications, there exists a need for a TBBPA predominant product having both low organic impurity and low ionic impurity. These low impurity TBBPA predominant products have particular application as flame retardants in polymers and plastics for the electronics industry.

A particularly useful process for enhancing the quality of a product predominant in TBBPA is disclosed in Application Ser. No. 614,372, filed Nov. 15, 1990, now U.S. Pat. No. 5,107,035.

There is also a need, due to impending environmental restrictions on the production and use of methyl bromide, for a process which substantially reduces the amount of methyl bromide formed as a coproduct when using methanol as reaction solvent. Accordingly, one object of this invention is to provide a facile economic means for substantially reducing the amount of methyl bromide coproduct formed without the need for substantial capital investment.

THE INVENTION

This invention provides, inter alia, a significant improvement in a process for preparing tetrabromobisphenol-A whereby a tetrabromobisphenol-A predominant product having a reduced amount of impurities is formed. The process comprises: (a) dissolving bisphenol-A in a methanol solvent containing up to about 5 weight percent water, wherein the ratio of methanol to bisphenol-A ranges from about 25 to about 43 moles of methanol per mole of bisphenol-A based on the total amount of methanol used and the total amount of bisphenol-A to be brominated; (b) adding to the solution in (a) from about 3.9 to about 4.2 moles of bromine per mole of bisphenol-A to be brominated while maintaining a reaction temperature in the range of from about 0° to about 40° C.; (c) after the bromination is substantially complete, precipitating the tetrabromobisphenol-A thus formed; and (d) purifying the precipitated tetrabromobisphenol-A so as to obtain a product predominant in tetrabromobisphenol-A containing less than about 20 ppm total ionic impurity.

Accordingly, it has been discovered that the amount of reaction solvent relative to the bisphenol-A to be brominated and the amount of water in that solvent has a beneficial impact on the quality of product that can be produced. It has also been found that such brominated product can be further purified by contacting the precipitated product with a quality enhancing amount of treated water, and heat treating the contacted product at a temperature and for a period of time which are sufficient to form a product having less than 20 ppm total ionic impurity and a reduced amount of organic impurity.

The improved process of the present invention provides, for the first time, a method for the production of a product predominant in tetrabromobisphenol-A (TBBPA) on a large scale at high yield having greatly reduced ionic and organic impurities. By greatly reduced is meant the ionic impurity in the recovered and dried product is preferably less than about 30 ppm, more preferably less than about 20 ppm, and most preferably less than about 10 ppm and the organic impurity is less than about 2 wt. %. For purposes of this invention, "total ionic impurity" means any of one or more of compounds represented by MBr wherein M is hydrogen, a metal, or an alkali or alkaline earth metal ion selected from the group consisting essentially of Ba, Ca, Fe, K, Na, Mg, and Mn. In a preferred embodiment, the ionic impurity is predominantly HBr (i.e. greater than about 50% by weight HBr). Organic impurities in the product reduced by the process of this invention include phenols; brominated phenols; alkylphenols; bromoalkylphenols; brominated alkylphenols; brominated bromoalkylphenols; mono-, di-, and tri-bromobisphenol-A; and the like.

In another embodiment, this invention provides a flame retardant composition comprising a product predominant in tetrabromobisphenol-A and containing less than about 10 ppm total ionic impurity and less than about 2.0 weight percent total organic impurity and a process therefor. The process comprises: (a) charging bisphenol-A and a first amount of methanol solvent to a reaction vessel wherein the methanol solvent contains less than about 5 weight percent water; (b) brominating the bisphenol-A by feeding bromine and, optionally, a second amount of methanol solvent containing less than about 5 weight percent water to the reaction vessel containing bisphenol-A and the first amount of methanol solvent provided that the ratio of methanol to bisphenol-A ranges from about 25 to about 43 moles of methanol per mole of bisphenol-A, said ratio being based on the first and second amounts of methanol fed and the total amount of bisphenol-A to be brominated; (c) maintaining a reaction temperature in the range of from about 0° to about 40° C. during the bromination of the bisphenol-A; (d) when the bromination is substantially complete, adding water to precipitate the tetrabromobisphenol-A thus formed; and (e) purifying the precipitated tetrabromobisphenol-A so as to obtain a product predominant in tetrabromobisphenol-A containing less than about 10 ppm total ionic impurity.

A further embodiment of this invention provides a process for preparing a flame retardant product predominant in tetrabromobisphenol-A while minimizing production of methyl bromide co-product. The process comprising: (a) dissolving bisphenol-A in a methanol solvent containing up to about 5 weight percent water, wherein the ratio of methanol to bisphenol-A ranges from about 25 to about 43 moles of methanol per mole of bisphenol-A based on the total amount of methanol used and the total amount of bisphenol-A to be brominated; (b) adding to the solution in (a) from about 3.9 to about 4.2 moles of bromine per mole of bisphenol-A to be brominated while maintaining a reaction temperature in the range of from about 0° to about 40° C. whereby the amount of methyl bromide co-product thus formed is minimized. By "minimized" is meant that the amount of methyl bromide thus formed is less than about 0.3 moles of methyl bromide per mole of tetrabromobisphenol-A product thus formed.

A key feature of this invention is the use of a methanol solvent containing less than 5 weight percent water, preferably from about 1 to less than about 5 weight percent water, more preferably, from about 1.5 to about 4 weight percent water, and most preferably about 4 weight percent water, and providing an amount of methanol solvent containing water whereby the ratio of the moles of methanol solvent to moles of bisphenol-A to be brominated ranges from about 25 to about 43 moles, most preferably from about 25 to about 35 moles of methanol per mole of bisphenol-A.

In the process of this invention, a first amount of methanol solvent containing water is charged to a reaction vessel. During or subsequent to the bromine addition step, a second amount of methanol may be added to the reaction vessel. The first amount of methanol charged should be sufficient to at least dissolve all of the bisphenol-A charged to the reaction vessel. Typically the first amount of methanol will be from about 75% to about 90% of the total amount of methanol used in the reaction. During the bromination reaction, the second amount of methanol added to the reaction vessel, provides sufficient solvent for maintaining under-brominated species in solution during the bromination reaction thereby decreasing the amount of such under-brominated species in the precipitated product. The second amount of methanol may range from about 10% to about 25% of the total amount of methanol used. By the term "under-brominated species" is meant mono-, di-, and tri-brominated bisphenol-A compounds. Accordingly, it has been found that increasing the amount of solvent relative to the bisphenol-A and under-brominated species in the reaction vessel will significantly decrease the amount of such under-brominated species in the tetrabromobisphenol-A product. While it is desirable to add the second amount of methanol to the reaction vessel during or subsequent to the bromine addition step, such second amount of methanol may be initially present in the reaction vessel, provided the total amount of methanol used is within the range of from about 25 to about 43 moles of methanol per mole of bisphenol-A to be brominated. In a particularly preferred embodiment, the bromine and second amount of methanol are charged to the reaction vessel during the bromine feed step, generally in accordance with the process as described in U.S. Pat. No. 5,017,728; U.S. Pat. No. 5,059,722, and/or U.S. Pat. No. 5,138,103 incorporated herein by reference as if fully set forth. Additional second amounts of methanol may be added to the reaction vessel after the bromine addition is complete in order to obtain the preferred amount of total methanol relative to the amount of bisphenol-A initially charged to the reaction vessel. It is to be understood of course, that the first and second amounts of methanol contain an amount of water ranging from about 1 to less than about 5 weight percent based on the total weight of methanol and water.

After charging the bisphenol-A and the methanol to the reaction vessel, bromine is fed to the reaction vessel so as to provide from about 3.9 to about 4.2 moles of bromine per mole of bisphenol-A to be brominated. Bromine may be fed as a liquid or as a vapor to the reaction vessel. Whether fed as a liquid or a vapor it is desirable, but not required, to dilute the bromine with solvent or an inert gas. Liquid bromine may be diluted with the second amount of methanol while feeding the bromine to the reaction vessel. Vaporized bromine may be diluted with nitrogen, steam, argon, and the like. It has been found, surprisingly, that vaporized bromine, whether diluted or not provides a TBBPA product having less impurities than when utilizing liquid bromine as the brominating agent.

While it is desirable to use sufficient bromine to provide 4 bromine atoms per molecule of bisphenol-A, utilizing less than a stoichiometric amount of bromine tends to reduce the amount of ionic impurity and increase the amount of under-brominated species in the tetrabromobisphenol-A product. However, it is more desirable to use an slight excess of bromine relative to the bisphenol-A so as to increase the yield of tetrabromobisphenol-A product which can be recovered.

The liquid bromine linear velocity feed rate has been found to also effect the purity of the tetrabromobisphenol-A product thus formed. It is preferred to use a bromine feed rate of greater than about 0.2 cm/sec. Preferably, the bromine feed rate should be greater than about 0.4 cm/sec; more preferably, at least about 2 cm/sec; and most preferably, at least about 3 to about 7 cm/sec. When feeding bromine as a vapor, the preferred linear velocity feed rate should be greater than about 85 cm/sec, more preferably greater than about 500 cm/sec, most preferably, at least about 1800 cm/sec. Regardless of whether liquid or vaporous bromine is fed, there is no real upper limit on the feed velocity for the bromine other than due to the physical constraints of the process equipment or the ability to adequately control reaction rate or temperature.

To a lesser extent, the agitation rate of the reaction mass may also have an effect on the purity of tetrabromobisphenol-A product thus formed. While the effect of agitation can generally be seen in lab scale reactions, on an industrial scale the agitation effect is less pronounced due to the difficulty of achieving similar agitation rates to the lab scale reactions.

During the bromination reaction, HBr is formed as a byproduct. Accordingly, for each mole of bromine reacted with bisphenol-A, one mole of HBr is formed. HBr is known to react with methanol to form methyl bromide. However, the process of this invention provides a means for decreasing the amount of methyl bromide thus formed. By adjusting the amount of water in the methanol, and by adjusting the post-bromination cook time and temperature, various amounts of methyl bromide co-product can be formed. It is believed, although this invention is not to be limited by any such theory, that water increases the formation of $H_3O^+Br^-$ thereby decreasing the concentration of HBr in the reaction mass which in turn reduces the rate of the methyl bromide formation reaction according to the following equations:

$$HBr + CH_3OH \rightarrow CH_3Br + H_2O \quad (I)$$

and $$HBr + H_2O \rightarrow H_3O^{+Br^-} \quad (II)$$

Being able to adjust the amount of methyl bromide formed during the bromination reaction is of particular importance due to the potential for new environmental regulations limiting methyl bromide production and use.

It has also been found that the methyl bromide formation reaction can be inhibited significantly by utilizing lower bromination reaction temperatures. At reaction temperatures above about 50° C., methyl bromide tends to form rapidly. For reduced methyl bromide production, temperatures in the range of from about 0° to about 50° C. are suitable. More preferably, the temperature is in the range of from about 0° to about 40° C., and most preferably from about 15° to about 30° C. If it is desired to increase the amount of methyl bromide thus formed, higher temperatures may also be used.

When utilizing temperatures of less than about 40° C., the rate of formation of the tetra-brominated species is reduced as compared to the rate at temperatures above 50° C. Accordingly, a cook time is generally required subsequent to the bromine addition step in order to convert under-brominated species such as dibromobisphenol-A and tribromobisphenol-A to tetrabromobisphenol-A. Factors which influence the cook time are the amount of solvent present, the amount of excess bromine used, and the bromination temperature. Cook times in the range of from about 0 5 to 2 hours have been found to be suitable when using 1 to 1.5% excess bromine, a methanol to bisphenol mole ratio of 33:1 and a temperature of from about 15° to about 30° C. The cook time for any set of conditions can be readily found empirically and is therefore not critical to this invention.

After the bromination reaction is substantially complete, sulfur dioxide is added to the reaction mass to destroy any remaining excess elemental bromine. Water is then added to the reaction mass to precipitate the tetrabromobisphenol-A product. The rate of addition and amount of water added to the reaction mass is not critical to this invention as such parameters are well known by those skilled in the art. Typically, sufficient water is added to the reaction mass to precipitate substantially all of the tetrabromobisphenol-A without precipitating undesirable amounts of under-brominated species. It is to be understood of course, that the recovery of usable product is related to the amount of product that can be precipitated from the reaction mass.

Another key feature of this invention is the step of contacting the TBBPA predominant product with a quality enhancing amount of treated water prior to heat treating product. The treated water is characterized as having a resistivity of greater than about 50,000 ohms, more preferably, greater than about 100,000 ohms, and most preferably greater than about 500,000 ohms. Such treated water can be prepared by contacting the water with commercially available ion exchange resin until the resistivity of the so treated water is greater than about 50,000 ohms. Higher resistivities can be obtained by treating the water in any one or more commercially available reverse osmosis units and subsequently contacting the water with an ion exchange resin. In the latter case, resistivities of greater than 500,000 ohms, typically greater than 1,000,000 ohms may be obtained. While it is desirable to contact the TBBPA predominant product with treated water having a resistivity as high as economically possible, good results may be obtained by contacting the TBBPA product with treated water having a resistivity at least about 50,000 ohms. The methods of preparing treated water having the foregoing resistivities is well known by those skilled in the art.

The amount of treated water used in contacting the TBBPA predominant product is that amount sufficient to enhance the quality of the product to the desired degree. Preferably, the product is contacted with at least about 0.1 grams of treated water per gram of product. More preferably, the product is contacted with at least about 0.2 grams of treated water per gram of product, and most preferably with about 0.3 to about 0.5 grams of water per gram of product. There is no real upper limit on the amount of treated water to use in contacting the product, however, economic considerations and manufacturing equipment limitations provide that only the amount of water required to enhance the quality of product to the desired degree need be used.

While it may be beneficial to contact the product with treated water at any stage of the process for preparing TBBPA, in general, the contacting need only be done after or during the procedure for separating the TBBPA predominant product from the reaction mass slurry. The reaction mass slurry is formed, by adding sufficient water to the reaction mass to precipitate the TBBPA predominant product. Removal of byproduct methyl bromide prior to filtering the product slurry is desirable. Such removal may be accomplished by well known techniques. The separation of the TBBPA predominant product from the reaction mass slurry may be accomplished by filtering or centrifuging the product solids. In the filtering or centrifuging operation, a major amount of aqueous HBr is removed from the solid product in the centrate or filtrate. However, residual HBr impurity remains in the solid product obtained from the separation process. The residual HBr impurity contributes to the total ionic impurity in the solid product.

Still another key feature of this invention is the step of heat treating the TBBPA predominant product at a temperature and for a period of time which are sufficient to reduce the amount of total ionic impurity in the thus treated product. When heat treating the product, the temperature is generally above about 110° C. Preferably, the temperature is in a range of from about 120° C. to about 180° C., and most preferably in a range of from about 130° C. to about 175° C. Higher or lower temperatures may also be used. However, the temperature should not be so high as to cause melting or degradation of the TBBPA predominant product. At a temperature lower than the preferred temperature, a longer heating time may be required to achieve the desired results.

The heat treating time required to obtain the enhanced quality product is related to the temperature used for the heat treating. At a temperature above about 120° C., the time for heat treating the product is preferably greater than about 10 seconds. A preferred residence time for heat treating a product predominant in TBBPA ranges from about 30 seconds to about 1 hour with the most preferred time ranging from about 5 minutes to about 30 minutes.

The time required may also depend on the equipment selected for the heat treating process. Equipment which may be useful in the process of this invention include the Wyssmont Turbo-Dryer ® and the Bepex Torusdisc ® Dryer, e.g. Torusdisc ® Model TDJ2611 having 218 square feet of heat transfer area and a 26 minute residence time at about 120° C. and the like. Those skilled in the art can readily select heat treating equipment based on the above residence times and temperatures in order to obtain the desired low impurity product.

Pressure is not critical to the process of this invention as the bromination reaction can be carried out at pressures ranging from subatmospheric to superatmospheric. It is less costly and more desirable to operate at about atmospheric pressure.

Particularly preferred processes for the production of a product predominant in TBBPA is described in Janzon et al., U.S. Pat. No. 3,929,907; Kleinschmit et al., U.S. Pat. No. 4,180,684; Mitchell, et al., U.S. Pat. No. 4,783,556; U.S. Pat. No. 4,909,997; and U.S. Pat. No. 5,059,722; McKinnie et al., U.S. Pat. No. 5,017,728; and Walter, U.S. Pat. No. 5,068,463 incorporated herein by reference. The process of the Mitchell et al. and McKinnie et al. patents produce a product generally having less than about 3 percent organic impurities. Typical organic impurities found in the product are partially brominated bisphenol compounds e.g. monobromobisphenol-A, dibromobisphenol-A and tribromobisphenol-A; partially brominated phenol compounds, e.g. bromophenol, dibromophenol, and tribromophenol; and brominated phenylphenols formed from traces of phenylphenol found in the bisphenol-A reactant. Traces of other organic compounds which may be found in the TBBPA predominant include but are not limited to 1-bromo-2-(3,5-dibromo-4-hydroxy-phenyl)-2-methoxypropane, 1,1-dibromo-2-(3,5-dibromo-4-hydroxyphenyl)-2-methoxypropane, 1,3-dibromo-2-(3,5-dibromo-4-hydroxyphenyl)-2-methoxypropane, and 1,1,3-tribromo-2-(3,5-dibromo-4-hydroxyphenyl)-2-methoxypropane.

While the organic impurities of the product produced by the foregoing processes are acceptably low for most flame retardant applications, the total ionic impurity in the product is typically about 60 ppm or more. It has now been discovered that TBBPA predominant product containing a total ionic impurity which is initially about 60 ppm or more can be treated by the process of this invention to obtain a TBBPA predominant product having less than about 30 ppm and most preferably, less than about 10 ppm total ionic impurity. In a particularly preferred embodiment, the product produced by this invention also contains less than about 3.0 weight percent organic impurity, most preferably, less than 2.0 weight percent organic impurity.

The process of this invention may be used to reduce the total ionic impurity content of a TBBPA predominant product before or after drying the product. It is particularly preferred, to separate the product from the reaction mass prior to contacting the product with a quality enhancing amount of treated water and heat treating the product. Alternatively, the product may be dried and ground to a powder having an average particle size of about 70 microns or less before contacting the product with treated water and heat treating the product. It is recognized, however, that the product may be dried and heat treated essentially simultaneously.

The following examples illustrate various features of this invention. For the purposes of this invention, plant process water is untreated water containing 150–200 ppm total dissolved solids.

EXAMPLE 1

Comparative Example—Temperature >40° C.

Tetrabromobisphenol-A is prepared generally in accordance with U.S. Pat. No. 4,783,556. For each run, methanol containing the amount of water indicated in Table 1 is used. The maximum temperature during the reaction and cook period is also indicated in Table 1. The percent yield of methyl bromide thus formed is given in column 4 of Table 1 and is based on a theoretical yield of 0.70 grams of methyl bromide per gram of tetrabromobisphenol-A formed.

TABLE 1

| Run # | $H_2O$ in Methanol (wt. %) | Maximum Temperature (°C.) | Methyl Bromide (% yield) |
|---|---|---|---|
| 1 | 2 | 67.5 | 42.6 |
| 2 | 5 | 70.2 | 33.6 |
| 3 | 8 | 72.0 | 28.3 |
| 4 | 11 | 73.4 | 24.1 |
| 5 | 14 | 74.2 | 21.1 |

In the foregoing runs, bromine is fed over 65 minutes at a rate of 95.2 kilograms per minute and additional methanol is fed at a rate of 47 kilograms per minute. After the bromination is complete, the product is cooked at reflux for 30 minutes at a pressure of 0.1 MPa.

Example 2 which illustrates the process of this invention utilizes maximum temperatures of 15° and 30° C.

EXAMPLE 2

Temperature below 40° C.

In a 500 mL 4-neck flask fitted with a -10° C. Friedrichs condenser, thermometer, mechanical stirrer and addition funnel with a dip tube and cooled in an ice bath was placed the amount of methanol and bisphenol-A indicated in Table 2. In runs 1 and 2, the methanol contained 11 wt. % water. In runs 3 and 4, the methanol contained 4 wt. % water. While stirring, the reaction mass was maintained at the temperatures indicated for each run in Table 2. Bromine was added through the dip tube to the reaction mass over the period of time indicated in Table 2. After completion of the bromine addition, the reaction mass was cooked at the temperature indicated for up to 3 hours and the percent yield of methyl bromide formed during the cook period was determined.

The amount of methyl bromide thus formed was determined by the use of gas chromatographic analysis according to the following procedure. Samples were removed by applying nitrogen pressure through the condenser and catching samples as the liquid rose up the diptube. Samples were taken directly into a cold mixture of 10 ml iso-octane and 10 ml water. The sample was immediately capped with a septum cap, shaken and the iso-octane layer analyzed on a 30 meter DB-5 capillary column, split injection, at 80° C. isothermal using an internal standard.

TABLE 2

| Reaction Conditions | Run #1 | Run #2 | Run #3 | Run #4 |
| --- | --- | --- | --- | --- |
| Temperature (°C.) | 15 | 30 | 15 | 30 |
| Bisphenol-A (grams) | 67.2 | 66.4 | 67.0 | 67.0 |
| Methanol used (mL, 100% basis) | 455 | 455 | 350 | 350 |
| Water added to methanol (mL) | 44 | 44 | 11.5 | 11.5 |
| Bromine added (grams) | 173 | 173 | 167 | 167 |
| $Br_2$ addition time (min.) | 20 | 10 | 15 | 12 |
| $CH_3Br$ formed (% yield) | <0.01 | 0.038 | 0.027 | 0.42 |
| (min. after $Br_2$ added) | (7 min.) | (10 min.) | (8 min.) | (10 min.) |
| $CH_3Br$ formed (% yield) | 0.037 | 0.24 | 0.15 | 1.38 |
| (min. after $Br_2$ added) | (87 min.) | (55 min.) | (35 min.) | (30 min.) |
| $CH_3Br$ formed (% yield) | 0.057 | 0.46 | 0.41 | 1.90 |
| (min. after $Br_2$ added) | (118 min.) | (114 min.) | (95 min.) | (60 min.) |
| $CH_3Br$ formed (% yield) | — | 0.74 | 0.56 | 2.70 |
| (min. after $Br_2$ added) | | (175 min.) | (140 min.) | (90 min.) |

In the foregoing runs, excess bisphenol-A was used in order to determine the rate at which methyl bromide is formed for the various reaction conditions.

Example 3, which is of this invention, illustrates the use of bromine vapor feed to the reaction vessel.

EXAMPLE 3

Bromine Vapor Feed Reactions

To a 2-liter 4-neck flask equipped with a −10° C. Friedrichs condenser, thermometer, mechanical stirrer, and 0.16 centimeter in diameter dip tube are added 180 grams (0.79 moles) of bisphenol-A and 880 mL of methanol containing 4 wt. % water. Bromine (513 grams, 3.2 moles) was fed with a peristaltic pump to a 1.8 meter, 0.63 centimeter outside diameter teflon tube held in hot water which was maintained at a temperature of >80° C. Bromine vapor thus generated was fed to the reaction flask over a 52 minute period and the temperature was maintained during the ({reaction at 28-32° C. by use of an ice bath. When all of the bromine had been added, additional methanol (175 mL) containing 4 wt. % water was added to the reaction flask and the mixture was stirred at 30° C. The overall methanol to bisphenol-A ratio was 32 moles of methanol per mole of bisphenol-A. A first sample of the homogenous mixture was taken 60 minutes after the bromine was added. The first sample was analyzed and indicated the presence of 0.03% yield of dibromophenol, 0.03% hydrolyzable impurities, 2.79% tribromobisphenol-A, and 97.18% tetrabromobisphenol-A. After an additional 30 minutes, a sample of liquid portion of the heterogenous mixture was analyzed and contained 2.17% tribromobisphenol-A. Water (700 mL) addition was begun immediately after taking the second sample and was complete in 20 minutes. The resulting orange mixture was filtered and the tetrabromobisphenol-A product was washed with 500 mL of deionized water. The product, thus isolated, was placed in a crystallizing dish and 1 mL of 56 wt % HBr was added. The product was then oven dried at 130° C for four hours. The dried product was analyzed as in Example 2 and indicated 99.24 wt. % tetra-bromobisphenol-A, an acetone color of 10 APHA, a TOHTO color of 20 APHA, an ionic bromide content of 0 ppm, and a hydrolyzable bromide content of 21 ppm.

The yield of brominated phenols, hydrolyzable impurities, tribromobisphenol-A, and TBBPA was determined by the use of gas chromatographic analysis according to the following procedure. A sample of the reaction mixture (0.5 mL) was diluted with one mL of methylene chloride, and shaken with 10 mL of water containing a small amount of sodium sulfite. The organic layer was separated and filtered, followed by evaporation of the methylene chloride solvent. The remaining solid was dissolved in 1 mL of pyridine and 1 mL of N,o-bis(trimethylsilyl)-trifluoroacetamide (BSTFA) added to silylate the sample. The sample was then analyzed on a gas chromatograph using a 61 centimeter long by 0.3175 centimeter outside diameter column of 5% OV-101 at a temperature of 100° to 300° C. which was heated at 10° C per minute.

EXAMPLE 4

Bromine Vapor Feed Reactions

In the next series of runs, the general procedure of Example 3 was used; however, the reaction temperature, methanol to bisphenol-A ratio, weight percent water in the methanol, and dip tube size were varied as indicated in the Table 3. The yield of impurities in the product contained in Table 3 were from analyses of samples of the homogenous reaction mixture. All analysis was performed generally in accordance with the procedure of Example 3.

TABLE 3

| Run # | $Br_2$ in nitrogen (wt. %) | Reaction Temperature (°C.) | Moles of MeOH per mole of bisphenol-A | Amount of $H_2O$ in methanol (wt. %) | Brominated phenols (% yield) | Hydrolyzables (% yield) | Diptube inside diameter (mm) |
| --- | --- | --- | --- | --- | --- | --- | --- |
| 1 | 30 | 60 | 34 | 2 | 0.030 | 0.045 | 1.57 |
| 2 | 30 | 60 | 27 | 2 | 0.050 | 0.063 | 1.57 |
| 3 | 30 | 15 | 42 | 11 | 0.027 | 0.010 | 1.57 |
| 4 | 30 | 30 | 42 | 11 | 0.021 | 0.021 | 1.57 |
| 5 | 100 | 67 | 27 | 2 | 0.052 | 0.063 | 1.57 |
| 6 | 100 | 67 | 27 | 2 | 0.045 | 0.062 | 1.57 |
| 7 | 90 | 67 | 27 | 2 | 0.055 | 0.060 | 1.57 |
| 8 | 100 | 67 | 27 | 2 | 0.052 | 0.076 | 0.86 |
| 9 | 50 | 67 | 27 | 2 | 0.047 | 0.064 | 0.86 |
| 10 | 100 | 67 | 27 | 2 | 0.070 | 0.080 | 3.96 |
| 11 | 100 | 20-25 | 27 | 2 | 0.039 | 0.064 | 0.86 |
| 12 | 30 | 20-25 | 27 | 2 | 0.017 | 0.016 | 0.86 |
| 13 | 100 | 20-25 | 41 | 2 | 0.024 | 0.027 | 0.86 |
| 14 | 100 | 67 | 27 | 2 | 0.060 | 0.069 | 1.57 |
| 15 | 100 | 20-25 | 27 | 2 | 0.040 | 0.057 | 1.57 |
| 16 | 30 | 66 | 27 | 2 | 0.050 | 0.064 | 1.57 |
| 17 | 36 | 30 | 27 | 4 | 0.013 | 0.014 | 1.57 |

TABLE 3-continued

| Run # | Br₂ in nitrogen (wt. %) | Reaction Temperature (°C.) | Moles of MeOH per mole of bisphenol-A | Amount of H₂O in methanol (wt. %) | Brominated phenols (% yield) | Hydrolyzables (% yield) | Diptube inside diameter (mm) |
| --- | --- | --- | --- | --- | --- | --- | --- |
| 18 | 100 | 55-60 | 27 | 2 | 0.055 | 0.064 | 1.57 |
| 19 | 100 | 30 | 42 | 11 | 0.031 | 0.022 | 1.57 |

In Example 5, the effect of liquid bromine fed rate to impurity formation is illustrated.

EXAMPLE 5

Liquid Bromine Feed Rate Effect on Impurities

Runs 30-34 were performed generally in accordance with Example 1. In this series of runs, the bromine feed rate ranged from 0.52 to 5.3 centimeters per second and the water in the methanol ranged from 2 to 11 wt. %. Methanol to bisphenol-A ratio was varied between 26.6 and 41.8 moles of methanol per mole of bisphenol-A.

TABLE 4

| Run # | Bromine velocity (cm/sec) | Reaction Temperature (°C.) | Moles of MeOH per mole of bisphenol-A | Amount of H₂O in methanol (wt. %) | Brominated phenols (% yield) | Hydrolyzables (% yield) | Agitator (RPM) | Diptube inside diameter (mm) |
| --- | --- | --- | --- | --- | --- | --- | --- | --- |
| 1 | 4.7 | 25 | 42 | 11 | 0.18 | 0.03 | 300 | 0.86 |
| 2 | 5.2 | 25-30 | 27 | 4 | 0.26 | 0.50 | 300 | 0.86 |
| 3 | 5.3 | 67 | 27 | 4 | 0.41 | 0.50 | 300 | 0.86 |
| 4 | 0.52 | 67 | 30 | 2 | 2.5 | 1.63 | 75 | 1.57 |
| 5 | 0.57 | 67 | 30 | 2 | 0.69 | 0.70 | 550 | 1.57 |

Examples 6, 7, and 8 illustrate the heat treating step in the absence of contacting the product with treated water.

EXAMPLE 6

Heat treatment without contacting with treated water

One vent of a lab oven was removed and a stirrer having an inverted ½ moon paddle was inserted into the oven through the vent. A 600 mL beaker was placed into the oven and the beaker was preheated to about the oven temperature. TBBPA product (20 grams) produced by the process of the Mitchell et al. U.S. Pat. No. 4,783,556 was filtered washed with plant process water and placed into the preheated beaker which in was the oven. During the heat treatment step, the product was stirred by hand. The product had an initial total ionic content of about 84 ppm HBr. The results of the heat treating runs are listed in Table 5. Samples 1-8 were previously dried before heat treating. Samples 9-10 were still wet with water prior to heat treating and had an initial total ionic content of 74 ppm.

TABLE 5

| Run No. | Time (min.) | Temp. (°C.) | Total Ionics (ppm) |
| --- | --- | --- | --- |
| 1 | 10 | 121-124[1] | 35 |
| 2 | 10 | 135-140[1] | 10 |
| 3 | 5 | 150-155[1] | 10 |
| 4 | 5 | 135[2] | 10 |
| 5 | 0.5 | 135[2] | 49 |
| 6 | 1.5 | 140[2] | 10 |
| 7 | 4 | 127[2] | 15 |
| 8 | 4 | 105[2] | 31 |
| 9 | 2.2 | 135[2] | 24 |
| 10 | 2.1 | 140[2] | 16 |

[1]Oven temperatures.
[2]TBBPA product temperatures.

In Runs 11-20, about 5 pounds of dry TBBPA predominant product produced by the process described in the Mitchell et al. patent were washed with plant process water. The product initially contained about 59 to about 62 ppm total ionic impurity and was dried at various temperatures in the dryers indicated. Samples of the product during the drying cycle were analyzed and the results are given in the following Tables 6 and 7.

TABLE 6

| | Wyssmont Turbo-Dryer | | |
| --- | --- | --- | --- |
| Run No. | Temp. (°C.)[3] | Time (min.) | Total Ionics (ppm) |
| 11 | 121 | 10 | 58 |
| | | 15 | 55 |
| | | 20 | 50 |
| | | 25 | 46 |
| | | 30 | 35 |
| 12 | 132 | 10 | 53 |
| | | 14 | 49 |
| | | 18 | 42 |
| | | 22 | 35 |
| | | 26 | 27 |
| 13 | 143 | 10 | 51 |
| | | 14 | 48 |
| | | 20 | 26 |
| | | 30 | 14 |
| 14 | 160 | 10 | 44 |
| | | 14 | 33 |
| | | 20 | 18 |
| | | 30 | 11 |
| 15 | 143 | 18 | 50 |
| | | 30 | 22 |
| | | 40 | 13 |
| | | 60 | 10 |
| 16 | 177 | 10 | 48 |
| | | 15 | 19 |
| | | 20 | 15 |
| | | 25 | 10 |
| | | 30 | 8 |

[3]Dryer air temperature.

TABLE 7

| | Bepex Torusdisc ® Dryer | | |
| --- | --- | --- | --- |
| Run No. | Temp. (°C.)[3] | Time (min.) | Total Ionics (ppm) |
| 17 | 149 | 5 | 49 |
| | | 9 | 41 |
| | | 11 | 34 |
| | | 18 | 21 |
| | | 31 | 20 |
| 18 | 177 | 3 | 39 |
| | | 6 | 22 |
| | | 10 | 17 |
| | | 50 | 14 |
| 19 | 163 | 6 | 29 |
| | | 8 | 19 |
| | | 12 | 15 |
| | | 22 | 19 |

TABLE 7-continued

| Run No. | Bepex Torusdisc ® Dryer | | |
|---|---|---|---|
| | Temp. (°C.)[3] | Time (min.) | Total Ionics (ppm) |
| | | 30 | 11 |
| 20 | 149 | 3 | 47 |
| | | 5 | 32 |
| | | 10 | 24 |
| | | 13 | 20 |
| | | 15 | 15 |
| | | 30 | 12 |

[3] Dryer steam temperature.

EXAMPLE 7

Heat treatment without contacting with treated water

A sample of TBBA product (100 grams) produced generally in accordance with the process of Mitchell et al. U.S. Pat. No. 4,783,556 having 66 ppm total ionics was slurried in 20wt. % methanol in plant process water. The TBBPA product was then filtered from the slurry and washed with about 200 mL of plant process water. After washing the product, the product was heat treated at 140° C. for 2.5 days. Total ionics after the heat treating step was 30 ppm.

EXAMPLE 8

Heat treatment without contacting with treated water

Tetrabromobisphenol-A was prepared generally in accordance with U.S. Pat. No. 4,783,556. A reaction flask was charged with 84.3 grams of bisphenol-A, and 500 mL of methanol. Bromine (79 mL) was added to the refluxing methanol over a period of 1 hour. The resulting reaction mass was stirred for 20 minutes while refluxing. Plant process water (170 mL) was added to pre-cipitate the product and form a product slurry. The TBBPA pro-duct was then filtered from the slurry and washed with about 200 mL of 20 wt. % methanol then 200 mL of plant process water. The washed product was reslurried in about 200 mL of 20 wt. % methanol in plant process water, filtered, and washed with about 20 mL of plant process water. Analysis of the washed wet cake indicated that the TBBPA product had a total ionic content of 40 ppm. The product was then heat treated at 140° C. for 16 hours Total ionics after heat treating was 27 ppm.

Examples 9 and 10 illustrate the improvement in product purity obtained when the product is contacted with treated water prior to heat treating the product.

EXAMPLE 9

Product contacted with treated water then heat treated

A sample of TBBPA product (100 grams) produced generally in accordance with the process of Mitchell et al. U.S. Pat. No. 4,783,556 having 66 ppm total ionics was slurried in 20 wt. % methanol in deionized water having a resistivity of about 100,000 ohms. The TBBPA product was then filtered from the slurry and washed with 200 mL of deionized water having a resistivity of about 100,000 ohms. After washing the product, the product was heat treated at 140° C. for 2.5 days. Total ionics after the heat treating step was less than 2 ppm.

EXAMPLE 10

Product contacted with treated water then heat treated

A sample of TBBPA product (100 grams) produced generally in accordance with the process of Mitchell et al. U.S. Pat. No. 4,783,556 having 62 ppm total ionics was slurried in 10 wt. % methanol in deionized water having a resistivity of about 100,000 ohms. The TBBPA product was then filtered from the slurry and washed with about 200 mL of deionized water having a resistivity of about 100,000 ohms. After washing the product, the total ionics were 46 ppm. The sample was separated into three portions and heat treated at different temperatures. Analysis of the product contacted with treated water and subsequently heat treated are given in Table 8.

TABLE 8

| Sample | Temperature (°C.) | Time (Hrs) | Total Ionics (ppm) |
|---|---|---|---|
| 1 | 120 | 4 | <8 |
| 2 | 60–65 | 5 | 49 |
| 3 | 70 | 22 | 40 |
| 4 | 120 | 22 | <2 |

The process of this invention is applicable to flame retardant products comprised predominantly of brominated compounds derived from compounds represented by the following:

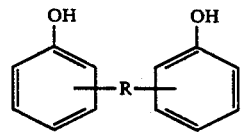

wherein R is a divalent aliphatic hydrocarbon group of 1–4 carbon atoms or a direct bond between two benzene rings. Representative examples are 4,4'-methylenebisphenol; 2,2'-methylenebisphenol; 2,4'-methylenebisphenol; 4,4'-ethylidenebisphenol; 2,2'-ethylidenebisphenol; 2,4'-ethylidenebisphenol; 2,2'-isopropylidenebisphenol; 2,4'-isopropylidenebisphenol; 4,4'-butylidenebisphenol; 2,2'-butylidenebisphenol; 4,4'-bisphenol; 2,2'-bisphenol; 2,4'-bisphenol and the like. These bisphenols can be substituted for the bisphenol-A, i.e., 4,4'-isopropylidenebisphenol, used in the foregoing description and examples of the present invention. All of the brominated products can be used as fire retardants in a broad range of organic materials normally susceptible to combustion in the presence of air and an ignition source.

Other variations are possible within the spirit and scope of the appended claims.

What is claimed is:

1. A process for preparing a flame retardant product predominant in tetrabromobisphenol-A comprising:
   a) dissolving bisphenol-A in a methanol solvent containing up to about 5 weight percent water, wherein the ratio of methanol to bisphenol-A ranges from about 25 to about 43 moles of methanol per mole of bisphenol-A based on the total amount of methanol used and the total amount of bisphenol-A to be brominated;
   b) adding to the solution in (a) from about 3.9 to about 4.2 moles of bromine per mole of bisphenol-A to be brominated while maintaining a reaction temperature in the range of from about 0° to about 40° C.; and
   c) after the bromination is substantially complete, precipitating the tetrabromobisphenol-A thus formed.

2. The process of claim 1 further comprising (i) contacting precipitated tetrabromobisphenol-A product with a quality enhancing amount of treated water and (ii) heat treating said product for a period of time and at a temperature which are sufficient to obtain a TBBPA predominant product having less than about 20 ppm of total ionic impurity wherein the ionic impurity is predominantly HBr.

3. The process of claim 2 wherein the heat treating temperature is in a range of from about 120° C. to about 170° C.

4. The process of claim 2 wherein the treated water has a resistivity of greater than about 100,000 ohms.

5. The process of claim 2 wherein the quality enhancing amount of treated water is more than about 0.2 grams of treated water per gram of product so contacted.

6. The process of claim 1 wherein the reaction temperature during the bromination is about 30° C.

7. The process of claim 1 wherein the amount of water in the methanol is about 4 weight percent.

8. The process of claim 3 wherein the amount of water in the methanol is about 4 weight percent.

9. The process of claim 1 wherein the methanol to bisphenol-A ratio ranges from about 25 to about 35 moles of methanol per mole of bisphenol-A.

10. The process of claim 1 wherein bromine is added to the solution at rate of greater than 0.2 cm/sec.

11. The process of claim 1 wherein bromine is added to the solution as a vapor.

12. A flame retardant composition prepared by the process of claim 2 comprising a product predominant in tetrabromobisphenol-A and containing less than about 10 ppm a ionic impurity and less than about 2.0 percent organic impurity wherein the ionic impurity is predominantly HBr.

13. A process for preparing a product predominant in bisphenol-A having less than about 20 ppm HBr impurity and less than about 2.0 percent organic impurity, which process comprises:
   a) charging bisphenol-A and a first amount of methanol solvent to a reaction vessel wherein the methanol solvent contains less than about 5 weight percent water;
   b) brominating the bisphenol-A by feeding bromine and, optionally, a second amount of methanol solvent containing less than about 5 weight percent water to the reaction vessel containing bisphenol-A and the first amount of methanol solvent provided that the ratio of methanol to bisphenol-A ranges from about 25 to about 43 moles of methanol per mole of bisphenol-A, said ratio being based on the first and second amounts of methanol fed and the total amount of bisphenol-A to be brominated;
   c) maintaining a reaction temperature in the range of from about 0° to about 40° C. during the bromination of the bisphenol-A; and
   d) when the bromination is substantially complete, adding water to precipitate the tetrabromobisphenol-A thus formed; and 14. The process of claim 13 further comprising (i) contacting precipitated tetrabromobisphenol-A product with a quality enhancing amount of treated water and (ii) heat treating said product for a period of time and at a temperature which are sufficient to obtain a TBBPA predominant product having less than about 20 ppm of total ionic impurity wherein the ionic impurity is predominantly HBr.

15. The process of claim 14 wherein the heat treating temperature is in a range of from about 120° C. to about 170° C.

16. The process of claim 15 wherein the treated water has a resistivity of greater than about 100,000 ohms.

17. The process of claim 16 wherein the quality enhancing amount of treated water is more than about 0.2 grams of treated water per gram of product so contacted.

18. The process of claim 17 wherein the reaction temperature during the bromination is about 30° C.

19. The process of claim 18 wherein the amount of water in the methanol is about 4 weight percent.

20. The process of claim 14 wherein the methanol to bisphenol-A ratio ranges from about 25 to about 35 moles of methanol per mole of bisphenol-A.

21. The process of claim 14 bromine is fed in at rate of greater than about 0.2 cm/sec.

22. The process of claim 21 wherein bromine is fed as a vapor.

23. A flame retardant composition prepared by the process of claim 21 comprising a product predominant in tetrabromobisphenol-A and containing less than about 10 ppm ionic impurity and less than about 2.0 percent organic impurity wherein the ionic impurity is predominantly HBr.

24. A process for preparing a flame retardant product predominant in tetrabromobisphenol-A while minimizing production of methyl bromide co-product, the process comprising:
   a) dissolving bisphenol-A in a methanol solvent containing up to about 5 weight percent water, wherein the ratio of methanol to bisphenol-A ranges from about 25 to about 43 moles of methanol per mole of bisphenol-A based on the total amount of methanol used and the total amount of bisphenol-A to be brominated;
   b) adding to the solution in (a) from about 3.9 to about 4.2 moles of bromine per mole of bisphenol-A to be brominated while maintaining a reaction temperature in the range of from about 0° to about 40° C. whereby the amount of methyl bromide co-product thus formed is minimized.

25. The process of claim 24 wherein the methanol to bisphenol-A ratio ranges from about 25 to about 35 moles of methanol per mole of bisphenol-A.

26. The process of claim 25 wherein the reaction temperature during the bromination is about 30° C.

27. The process of claim 26 wherein the amount of water in the methanol is about 4 weight percent.

* * * * *